United States Patent [19]

Takanaka

[11] Patent Number: 5,349,198
[45] Date of Patent: Sep. 20, 1994

[54] BEAM SUPPLY DEVICE

[75] Inventor: Masao Takanaka, Tokyo, Japan

[73] Assignee: Mitsubishi Denki Kabushiki Kaisha, Tokyo, Japan

[21] Appl. No.: 90,306

[22] Filed: Jul. 12, 1993

[30] Foreign Application Priority Data

Jul. 15, 1992 [JP] Japan .................. 4-188124

[51] Int. Cl.$^5$ ................. A61N 5/00; H01J 37/147
[52] U.S. Cl. ............................................. 250/492.3
[58] Field of Search .............. 250/492.3, 398, 396 ML

[56] References Cited

U.S. PATENT DOCUMENTS 4,870,287  9/1989  Cole et al. ............. 250/492.3
5,260,581 11/1993  Lesyna et al. ............. 250/492.3

FOREIGN PATENT DOCUMENTS 64-44899  2/1989  Japan ............. 250/396 ML

Primary Examiner—Jack I. Berman
Attorney, Agent, or Firm—Wolf, Greenfield & Sacks

[57] ABSTRACT

A beam supply device for supplying a particle or radiation beam to therapy or experiment equipment includes a beam generation device 1, a pre-branching beam transportation device 2, a rotatable deflection electromagnet 3, a rotatable beam transportation device 4, and a plurality of beam utilization rooms 5 disposed around the rotational axis of the rotatable deflection electromagnet 3 at a predetermined distance therefrom. The rotatable deflection electromagnet 3 and the rotatable beam transportation device 4 are rotated together to a predetermined rotational angle, such that the beam is guided to the room in which the beam is to be utilized.

3 Claims, 4 Drawing Sheets

BEAM SUPPLY DEVICE

BACKGROUND OF THE INVENTION

This invention relates to beam supply devices for supplying proton beams, heavy particles beams, etc., to devices which utilizes such beams, such as cancer therapy equipment and experimental radiation apparatus.

FIG. 5 is a cut-away perspective view of a conventional beam supply device. The beam (e.g., a proton beam or a heavy particle beam) generated by the beam generation device 1 (e.g., a synchrotron) is guided to the branch point by means of a pre-branching beam transportation device 2. At the branch point is disposed a branching deflection electromagnet 11a, which, when excited, generates a magnetic field for deflecting the beam by means of the Lorentz force. If the branching deflection electromagnet 11a is not excited and the interpole magnetic field thereof is null, the Lorentz force does not act upon the beam and the beam proceeds straight into a beam transportation device 12a and is guided horizontally into a beam utilization room 5a in front of the beam generation device 1. On the other hand, when the deflection electromagnets 11a and 11b are excited, the beam is first deflected upward by the branching deflection electromagnet 11a and then horizontally by the deflection electromagnet 11b, the beam being guided through the beam transportation device 12b, which may be a pre-branching type beam transportation device. If the branching deflection electromagnet 11c is excited, the beam is further deflected downward, guided through a beam transportation device 12c, and led into the beam utilization room 5a. On the other hand, if the branching deflection electromagnet 11c is not excited, the beam proceeds straight through a beam transportation device 12d. The beam is further deflected by an excited deflection electromagnet 11d, guided through the vertical extension of the beam transportation device 12d, and thence led into a beam utilization room 5b which is situated on the downstream side of the beam utilization room 5a.

The conventional beam supply device of FIG. 5 has the following disadvantage. The arrangement requires as many beam transportation devices as there are beam orbits leading into the beam utilization rooms. The beam transportation devices are expensive. If a large number of the beam utilization rooms must be provided, or a number of beam incident angles must be provided for each beam utilization room, the overall installation cost of the beam supply device becomes substantial.

SUMMARY OF THE INVENTION

It is therefore an object of this invention to provide a beam supply device by which the number of expensive beam transportation devices for supplying the beam to a plurality of beam utilization rooms can be reduced, thereby substantially reducing the overall installation cost thereof.

The above object is accomplished in accordance with the principle of this invention by a beam supply device for supplying a particle or radiation beam to a therapy experiment equipment which comprises: a beam generation means for generating a beam; a pre-branching beam transportation device coupled to the beam generation means for transporting the beam generated by the beam generation means to a predetermined point; a rotatable deflection electromagnet disposed at the predetermined point for deflecting the beam by a predetermined angle; a plurality of beam utilization rooms disposed around the rotational axis of the rotatable deflection electromagnet at a predetermined distance therefrom; a rotatable beam transportation device for guiding the beam deflected by the rotatable deflection electromagnet to one of the beam utilization rooms; and rotation means for rotating the rotatable deflection electromagnet and the rotatable beam transportation device around a rotational axis of the rotatable deflection electromagnet to a predetermined rotational angle, thereby selectively guiding the beam generated by the beam generation means to a selected one of the beam utilization rooms.

Preferably, the rotatable deflection electromagnet includes means for selectively turning on and off an excitation thereof; the beam supply device further comprising: a beam transportation device coupled to the rotatable deflection electromagnet to form a downstream extension of the pre-branching beam transportation device; and a beam utilization room disposed at a downstream end of the beam transportation device.

Still preferably, the rotatable deflection electromagnet includes means for selectively turning on and off an excitation thereof and the beam supply device further comprises: a beam transportation device coupled to the rotatable deflection electromagnet to form a downstream extension of the pre-branching beam transportation device, the beam transportation device guiding the beam to a second predetermined point; a second rotatable deflection electromagnet disposed at the second predetermined point for deflecting the beam by a predetermined angle; a plurality of second beam utilization rooms disposed around the rotational axis of the second rotatable deflection electromagnet at a predetermined distance therefrom; a second rotatable beam transportation device for guiding the beam deflected by the second rotatable deflection electromagnet to one of the second beam utilization rooms; and second rotation means for rotating the second rotatable deflection electromagnet and the second rotatable beam transportation device around a rotational axis of the second rotatable deflection electromagnet to a predetermined rotational angle, thereby selectively guiding the beam generated by the beam generation means and proceeding through the rotatable deflection electromagnet and deflected by the second rotatable deflection electromagnet to a selected one of the second beam utilization rooms.

BRIEF DESCRIPTION OF THE DRAWINGS

The features which are believed to be characteristic of this invention are set forth with particularity in the appended claims. The structure and method of operation of this invention itself, however, will be best understood from the following detailed description, taken in conjunction with the accompanying drawings, in which:

In the drawings, like reference numerals represent like or corresponding parts or portions.

DETAILED DESCRIPTION OF THE PREFERRED EMBODIMENTS

Referring now to the accompanying drawings, the preferred embodiments of this invention are described.

Figure 1:
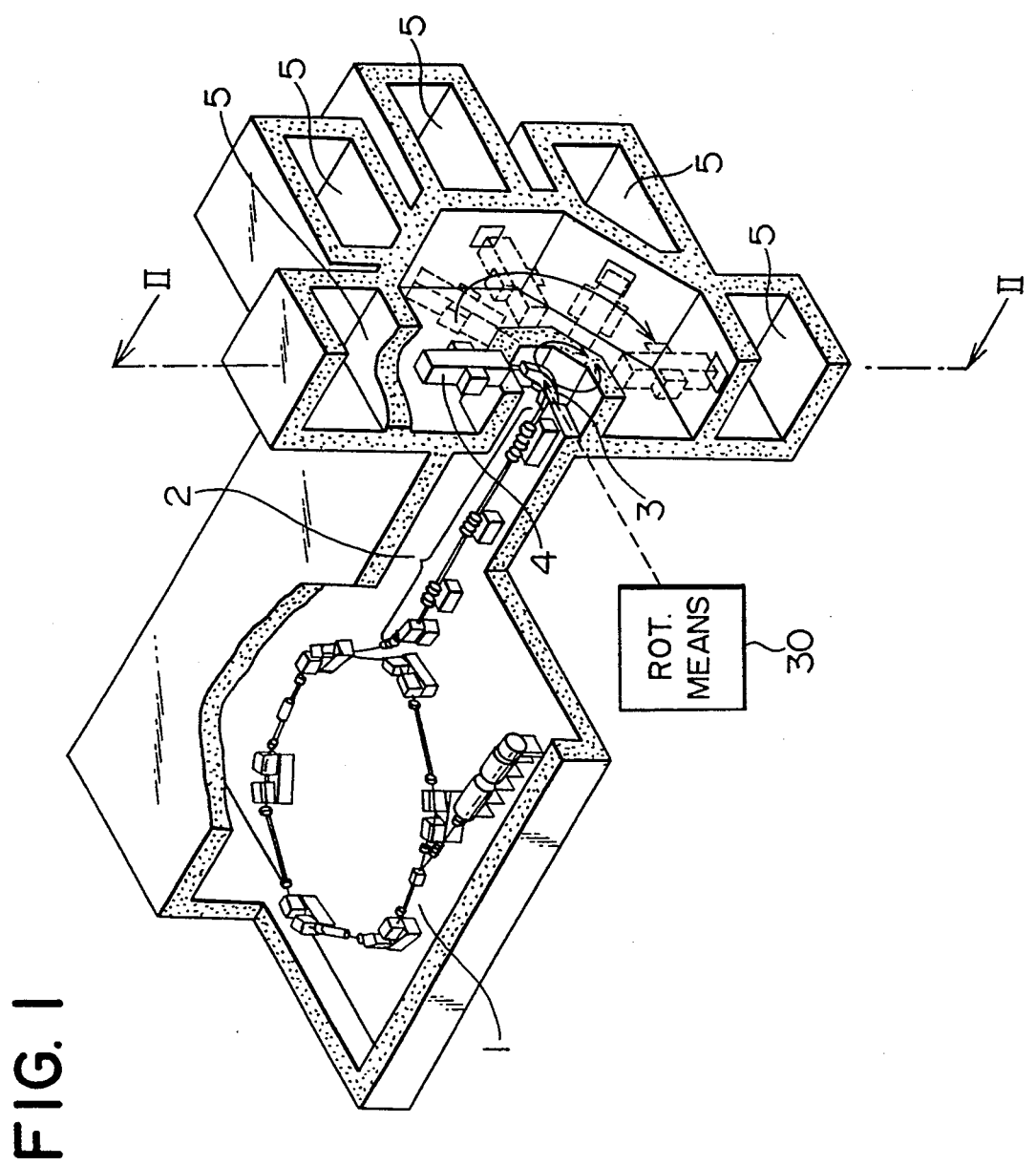
FIG. 1 is a cut-away perspective view of a beam supply device according to this invention.
Figure 2:
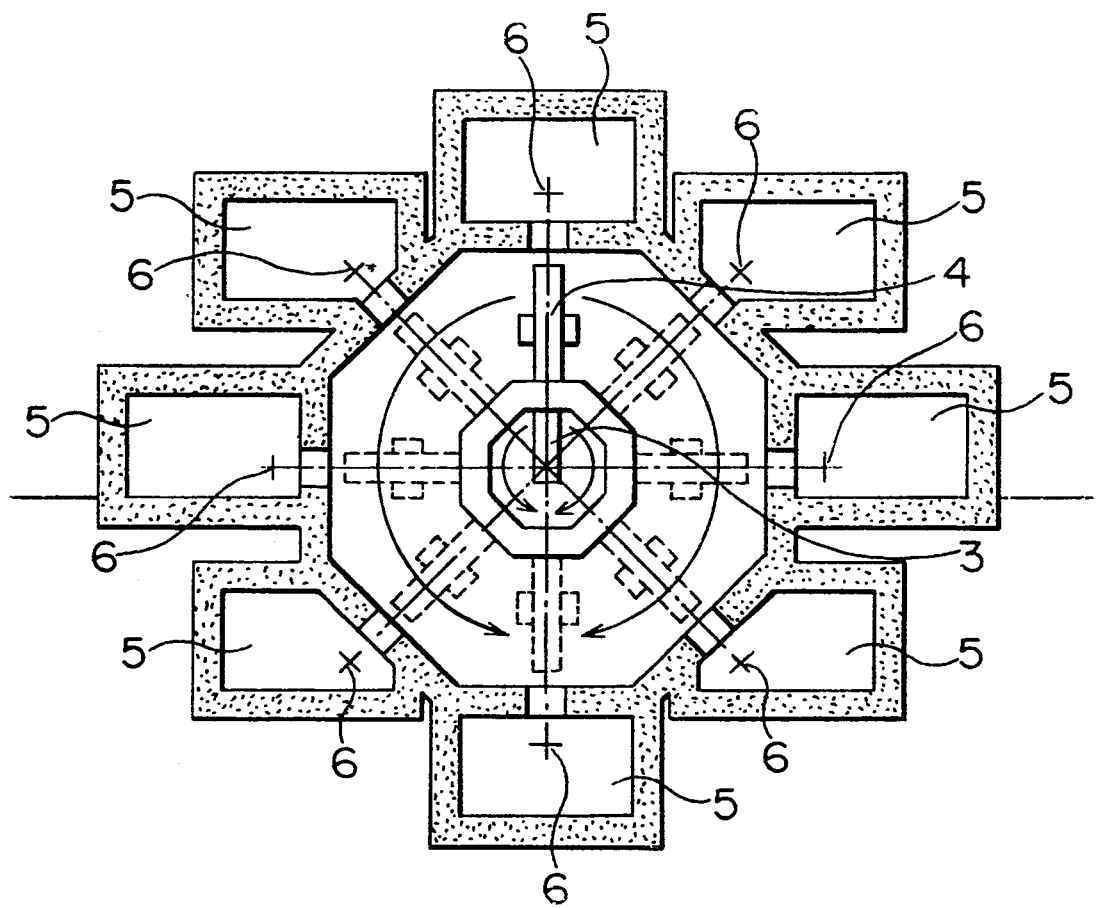
FIG. 2 is a cross-wise sectional view of the beam supply device of FIG. 1 along line A—A in FIG. 1.

FIG. 1 is a cut-away perspective view of a beam supply device according to this invention. FIG. 2 is a cross-wise sectional view of the beam supply device of FIG. 1 along line A—A in FIG. 1.

To the beam generation device 1 is connected a pre-branching beam transportation device 2, the primary components of which are deflection electromagnets, quadrupole electromagnets, vacuum containers, vacuum exhaust devices, and beam diagnosis devices. The pre-branching beam transportation device 2 transports the beam generated by the beam generation device 1 to the branching or deflection point of the beam orbit.

At the branching point (i.e., the deflection point) of the beam orbit is disposed a rotational switching device including a rotatable deflection electromagnet 3 with a deflection angle of 90 degrees, the upstream end of which is coupled to the pre-branching beam transportation device 2. The switching device switches (i.e., changes) the direction of the beam by rotating the rotatable deflection electromagnet 3 by means of a rotation means 30. A rotatable beam transportation device 4, coupled to the downstream end of the rotatable deflection electromagnet 3, is rotated together with the rotatable deflection electromagnet 3 around the rotational axis of the rotatable deflection electromagnet 3. A plurality of beam utilization rooms 5 are disposed around the rotational axis of the rotatable deflection electromagnet 3 at a predetermined distance therefrom (see FIG. 2). In the case of this embodiment, eight rooms are disposed to form an octagon around the rotational axis of the rotatable deflection electromagnet 3. The sides of the respective beam utilization rooms 5 facing the rotational axis of the rotatable deflection electromagnet 3 (i.e., the floor of the top room, the inner side walls of the middle rooms, and the ceiling of the bottom room) may form a regular octagon around the rotational axis of the rotatable deflection electromagnet 3. Through each side of the beam utilization rooms 5 facing the axis of the rotatable deflection electromagnet 3 is made a hole, such that when the rotatable beam transportation device 4 is directed toward the hole, the beam deflected by the rotatable deflection electromagnet 3 and transported through the rotatable beam transportation device 4 is led into the room 5 through the hole and utilized at the utilization point 6 of the room. The utilization points 6 of the beam utilization rooms 5 are substantially at an equal distance from the rotational axis of the rotatable deflection electromagnet 3.

The method of operation of the beam supply device of FIGS. 1 and 2 is as follows. The beam such as a proton beam or a heavy particle beam emitted from the beam generation device 1 is guided to the deflection point through the pre-branching beam transportation device 2. At the branching point the beam is deflected by the rotatable deflection electromagnet 3 into a direction at right angles with the axis of the pre-branching beam transportation device 2. The rotational angle of the rotatable deflection electromagnet 3 determines the room in which the beam is utilized. The rotatable deflection electromagnet 3 and the rotatable beam transportation device 4 are rotated together to a predetermined angle by means of the rotation means 30, such that the beam axis of the rotatable beam transportation device 4 is aligned with the utilization point 6 of the room 5 in which the beam is currently utilized.

The utilization room 5 to which the beam is supplied can be switched by rotating the rotatable deflection electromagnet 3 and the rotatable beam transportation device 4 by means of the rotation means 30. Thus, a single rotatable beam transportation device 4 is capable of transporting the beam to a plurality of rooms disposed around the rotational axis of the rotatable deflection electromagnet 3. The number of expensive beam transportation devices can thus be reduced.

It is to be noted that the rotatable beam transportation device 4 may include a part of the radiation device of the cancer therapy equipment (e.g., the wobbler electromagnet, the beam scatterer, the beam collimater and a part of the X-ray positioning device), or a part of the measurement device of the radiation experiment apparatus (e.g., the beam scatterer, beam collimator, and the measurement devices).

Further, in the case of the above embodiment, the rotatable beam transportation device 4 is rotated integrally with the rotatable deflection electromagnet 3 by means of the rotation means 30, However, the rotatable beam transportation device 4 may be rotated by a separate rotation means. Furthermore, the rotatable beam transportation device 4 may be formed of several parts which are rotated individually. For example, in the case of the cancer therapy equipment, the part of the rotatable beam transportation device 4 consisting of the elements used during beam radiation (e.g., the wobbler electromagnet, the beam scatterer, and the beam collimator) and the part of the rotatable beam transportation device 4 consisting of the elements used when no beam is radiated (e.g., the positioning device) may be rotated separately.

Furthermore, in the case of the embodiment of FIGS. 1 and 2, the utilization point 6 of the respective beam utilization rooms 5 are disposed around the rotational axis of the rotatable deflection electromagnet 3 at points which substantially form the eight vertexes of a regular octagon. However, this is not necessary. The only necessary condition is that the utilization points 6 of the respective beam utilization rooms 5 are substantially at an equal distance from the rotational axis of the rotatable deflection electromagnet 3.

Still further, in the case of the above embodiment, the deflection angle of the rotatable deflection electromagnet 3 is 90 degrees. However, the deflection angle may be less or greater than 90 degrees. When, for example, the deflection angle is less than 90 degrees, the beam can be directed along any line (generatrix) upon the cone surface whose rotational axis agrees with the rotational axis of the rotatable deflection electromagnet 3 and whose apex is at the branching point (deflection point). Then, the utilization points of the beam utilization rooms are to be disposed on the cone surface substantially at an equal distance from the apex of the cone.

Still further, in the case of the embodiment of FIGS. 1 and 2, the pre-branching beam transportation device 2, the rotatable deflection electromagnet 3, the rotatable beam transportation device 4, the beam utilization rooms 5, etc., are arranged in such positional relationships that the beam is incident upon the branching point (deflection point) horizontally. The horizontal incidence upon the deflection point, however, is not necessary. The beam from the beam generation device 1 may be transported through a pre-branching beam transportation device 2 which is inclined.

Figure 3:
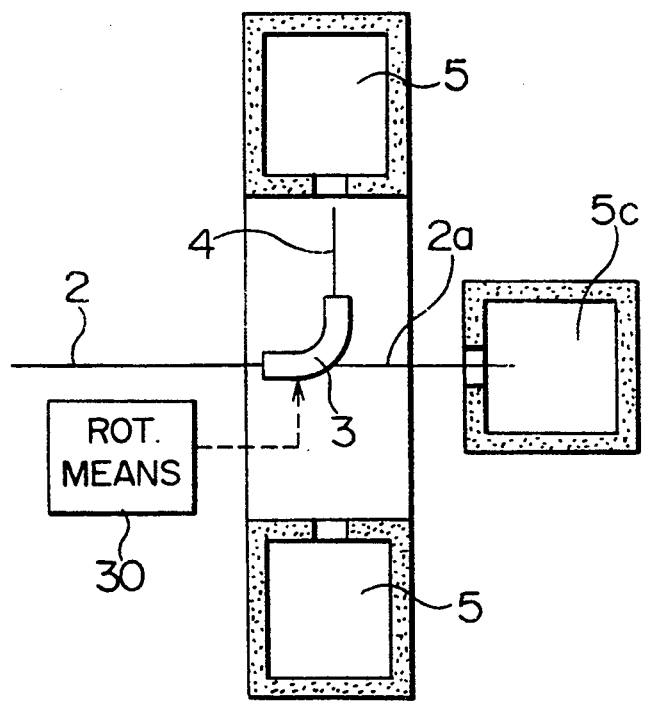
FIG. 3 is a schematic longitudinal partial sectional view of another beam supply device according to this invention.

FIG. 3 is a schematic longitudinal partial sectional view of another beam supply device according to this invention. In the case of the embodiment of FIG. 3, a beam transportation device 2a having a longitudinal axis agreeing with that of the pre-branching beam transportation device 2 is coupled to the rotatable deflection electromagnet 3, and the excitation of the rotatable deflection electromagnet 3 may selectively turned on and off. At the downstream end of the beam transportation device 2a is disposed a beam utilization room 5c having a hole formed through a wall facing the rotatable deflection electromagnet 3. The end of the beam transportation device 2a extends into the beam utilization room 5c.

When the rotatable deflection electromagnet 3 is not excited, the beam guided through the pre-branching beam transportation device 2 proceeds straight through the rotatable deflection electromagnet 3 and is guided through the beam transportation device 2a into the beam utilization room 5c. The operation of the beam supply device of FIG. 3 when the rotatable deflection electromagnet 3 is excited is the same as that of the beam supply device of FIGS. 1 and 2.

Figure 4:
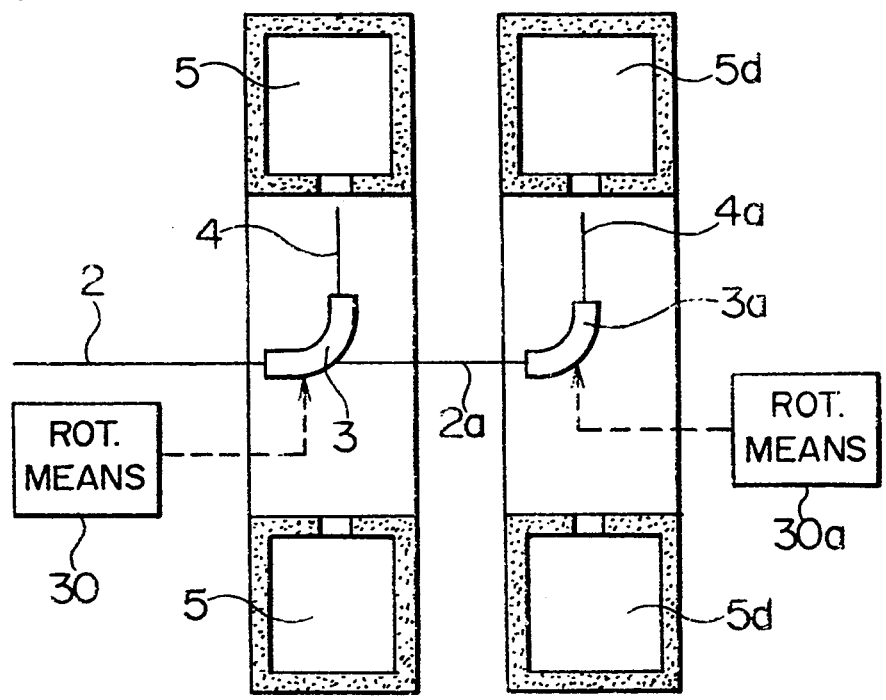
FIG. 4 is a schematic longitudinal partial sectional view of still another beam supply device according to this invention.

FIG. 4 is a schematic longitudinal partial sectional view of still another beam supply device according to this invention. The embodiment of FIG. 4 is similar to that of FIG. 3. However, in the case of the embodiment of FIG. 4, instead of the beam utilization room 5c, a plurality of beam utilization rooms 5d are arranged at the downstream side of the beam utilization rooms 5. A beam transportation device 2a having a longitudinal axis agreeing with the pre-branching beam transportation device 2 and forming an extension of the pre-branching beam transportation device 2 is coupled to the rotatable deflection electromagnet 3, and the rotatable deflection electromagnet 3a coupled to the downstream end of the beam transportation device 2a deflects the beam at right angles into the rotatable beam transportation device 4a. The structure and method of operation of the rotatable deflection electromagnet 3a, the rotatable beam transportation device 4a, and the beam utilization rooms 5d are similar to those of the rotatable deflection electromagnet 3, the rotatable beam transportation device 4, and the beam utilization rooms 5 of FIGS. 2 and 3. The excitation of the rotatable deflection electromagnet 3 may be selectively turned on and off. The rotatable deflection electromagnet 3a and the rotatable beam transportation device 4a are rotated by the rotation means 30a, independently of the rotatable deflection electromagnet 3 and the rotatable beam transportation device 4 which are rotated by the rotation means 30.

Figure 5:
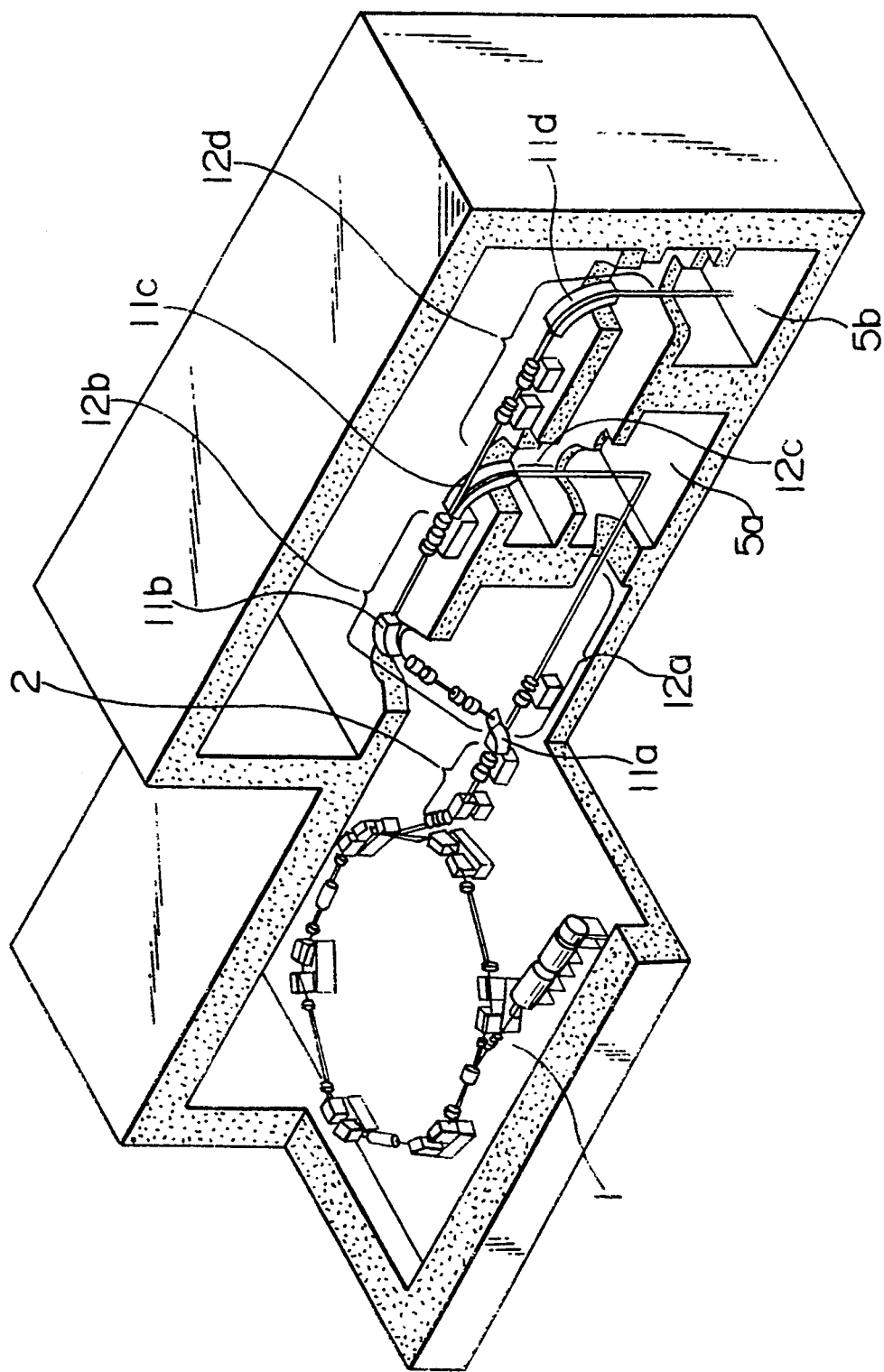
FIG. 5 is a cut-away perspective view of a conventional beam supply device.

When the rotatable deflection electromagnet 3 is excited, the beam is deflected into one of the beam utilization rooms 5 at the upstream side. When, on the other hand, the rotatable deflection electromagnet 3 is not excited, the beam proceeds straight through the rotatable deflection electromagnet 3 and the beam transportation device 2a, and is deflected by the rotatable deflection electromagnet 3a into one of the beam utilization rooms 5d at the downstream side. This tandem arrangement of the utilization rooms of the beam supply device of FIG. 4 permits a large number of beam utilization rooms served by a small number of beam transportation devices. It is possible to add further sets of the beam utilization rooms at the downstream side of the rooms 5d, guiding the beam thereto by means of an arrangement similar to the beam transportation device 2a, the rotatable deflection electromagnet 3a, and the rotatable beam transportation device 4a. Alternatively, a single room configuration (the beam transportation device 2a and the beam utilization room 5c of FIG. 3) may be added to the downstream side of the rooms 5d. It is further noted that the conventional beam branching method of the beam supply device of FIG. 5 may also be combined with the beam branching method according to this invention.

What is claimed is:

1. A beam supply device for supplying a particle or radiation beam to a therapy or experiment equipment comprising:
   beam generation means for generating a beam;
   a pre-branching beam transportation device coupled to said beam generation means for transporting said beam generated by said beam generation means to a predetermined point;
   a rotatable deflection electromagnet disposed at said predetermined point for deflecting said beam by a predetermined angle;
   a plurality of beam utilization rooms disposed around said rotational axis of said rotatable deflection electromagnet at a predetermined distance therefrom;
   a rotatable beam transportation device for guiding said beam deflected by said rotatable deflection electromagnet to one of said beam utilization rooms; and
   rotation means for rotating said rotatable deflection electromagnet and said rotatable beam transportation device around a rotational axis of said rotatable deflection electromagnet to a predetermined rotational angle, thereby selectively guiding said beam generated by said beam generation means to a selected one of said beam utilization rooms.

2. A beam supply device as claimed in claim 1, wherein: said rotatable deflection electromagnet includes means for selectively turning on and off an excitation thereof; said beam supply device further comprising: a beam transportation device coupled to said rotatable deflection electromagnet to form a downstream extension of said pre-branching beam transportation device; and a beam utilization room disposed at a downstream end of said beam transportation device.

3. A beam supply device as claimed in claim 1, wherein: said rotatable deflection electromagnet includes means for selectively turning on and off an excitation thereof; said beam supply device further comprising:
   a beam transportation device coupled to said rotatable deflection electromagnet to form a downstream extension of said pre-branching beam transportation device, said beam transportation device guiding said beam to a second predetermined point;
   a second rotatable deflection electromagnet disposed at said second predetermined point for deflecting said beam by a predetermined angle;
   a plurality of second beam utilization rooms disposed around said rotational axis of said second rotatable deflection electromagnet at a predetermined distance therefrom;
   a second rotatable beam transportation device for guiding said beam deflected by said second rotatable deflection electromagnet to one of said second beam utilization rooms; and second rotation means for rotating said second rotatable deflection electromagnet and said second rotatable beam transportation device around a rotational axis of said second rotatable deflection electromagnet to a predetermined rotational angle, thereby selectively guiding said beam generated by said beam generation means and proceeding through said rotatable deflection electromagnet and deflected by said second rotatable deflection electromagnet to a selected one of said second beam utilization rooms.

* * * * *